United States Patent
Finlay

(10) Patent No.: US 8,673,223 B1
(45) Date of Patent: Mar. 18, 2014

(54) FAN POWERED AIR FRESHENER AUTOMOBILE VISOR CLIP

(75) Inventor: Nathaniel Finlay, Lehi, UT (US)

(73) Assignee: American Covers, Inc., Draper, UT (US)

( * ) Notice: Subject to any disclaimer, the term of this patent is extended or adjusted under 35 U.S.C. 154(b) by 85 days.

(21) Appl. No.: 13/282,035

(22) Filed: Oct. 26, 2011

Related U.S. Application Data

(60) Provisional application No. 61/408,263, filed on Oct. 29, 2010.

(51) Int. Cl.
*A61L 9/04* (2006.01)

(52) U.S. Cl.
USPC .............................................. 422/124; 239/34

(58) Field of Classification Search
USPC .................................... 422/124, 120; 239/34
See application file for complete search history.

(56) References Cited

U.S. PATENT DOCUMENTS

| | | | |
|---|---|---|---|
| D176,671 S | 4/1876 | Myers | |
| 369,878 A | 9/1887 | Palmer | |
| 1,171,737 A | 2/1916 | Madigan | |
| D140,109 S | 1/1945 | Pierce | |
| 2,642,248 A | 6/1953 | Semon | |
| 2,733,333 A | 1/1956 | Peters | |
| D177,826 S | 5/1956 | Katz | |
| D178,237 S | 7/1956 | Katz | |
| 3,239,145 A | 3/1966 | Aurelio | |
| 3,456,106 A | 7/1969 | Gluschkin Mischa | |
| 3,552,632 A | 1/1971 | Wilson | |
| 3,655,129 A | 4/1972 | Seiner | |
| 3,847,305 A | 11/1974 | Tobin | |
| 3,948,445 A | 4/1976 | Andeweg | |
| 3,971,858 A | 7/1976 | Collier et al. | |
| D246,986 S | 1/1978 | Costello | |
| 4,084,079 A | 4/1978 | Costello | |
| D250,041 S | 10/1978 | Schimanski | |
| 4,149,675 A | 4/1979 | Van Breen et al. | |
| 4,184,099 A | 1/1980 | Lindauer et al. | |
| 4,226,944 A | 10/1980 | Stone et al. | |
| D258,511 S | 3/1981 | Ashton | |
| 4,280,649 A | 7/1981 | Montealegre | |
| 4,301,949 A | 11/1981 | Palson et al. | |
| 1,683,545 A | 9/1982 | Harris | |
| 4,382,548 A | 5/1983 | Van de Heijden | |

(Continued)

FOREIGN PATENT DOCUMENTS

| | | |
|---|---|---|
| CA | 2077251 | 5/1993 |
| EP | 0 348 970 | 1/1990 |

(Continued)

OTHER PUBLICATIONS

About.Com Housekeeping, http://housekeeping.about.com/od/pr . . . affresh, Febrezee Noticeables, accessed Oct. 2, 2008, 2 pages.

(Continued)

*Primary Examiner* — Sean E Conley
(74) *Attorney, Agent, or Firm* — Thorpe North & Western LLP

(57) ABSTRACT

A portable powered air freshener includes an air displacement mechanism carried by a housing including a fan. A scent capsule is carried by the housing and has a chamber containing a fragrant material and a permeable membrane through which a fragrance of the fragrant material can permeate over time.

23 Claims, 8 Drawing Sheets

(56) References Cited

U.S. PATENT DOCUMENTS

| | | |
|---|---|---|
| 4,391,781 A | 7/1983 | Van Lit |
| 4,517,326 A | 5/1985 | Cordts et al. |
| 4,549,693 A | 10/1985 | Barlics |
| 4,594,380 A | 6/1986 | Chapin et al. |
| D286,323 S | 10/1986 | Haworth |
| 4,638,057 A | 1/1987 | Takahashi et al. |
| 4,649,046 A | 3/1987 | Kross |
| 4,703,070 A | 10/1987 | Locko et al. |
| RE32,834 E | 1/1989 | Cordts et al. |
| 4,808,347 A | 2/1989 | Dawn |
| 4,840,773 A | 6/1989 | Wade |
| 4,849,606 A * | 7/1989 | Martens et al. ............... 392/390 |
| 4,874,129 A | 10/1989 | DiSapio et al. |
| 4,880,690 A | 11/1989 | Szycher et al. |
| 4,950,542 A | 8/1990 | Barker |
| 4,968,456 A | 11/1990 | Muderlak et al. |
| 5,008,115 A | 4/1991 | Lee et al. |
| 5,019,434 A | 5/1991 | Matsumoto |
| 5,034,222 A | 7/1991 | Kellett et al. |
| D319,781 S | 9/1991 | Halm et al. |
| 5,050,798 A | 9/1991 | Sullivan |
| D322,558 S | 12/1991 | Halm et al. |
| 5,071,704 A | 12/1991 | Fischel-Ghodsian |
| 5,114,625 A | 5/1992 | Gibson |
| 5,120,583 A | 6/1992 | Garcia |
| 5,178,327 A | 1/1993 | Palamand et al. |
| 5,180,107 A | 1/1993 | Lindauer |
| 5,193,445 A | 3/1993 | Ferguson |
| D334,975 S | 4/1993 | Bunce |
| 5,220,636 A | 6/1993 | Chang |
| D338,519 S | 8/1993 | Peterson |
| 5,234,162 A | 8/1993 | Sullivan |
| 5,240,487 A * | 8/1993 | Kung ............................. 96/222 |
| D349,157 S | 7/1994 | Rymer |
| D350,192 S | 8/1994 | Patel et al. |
| 5,368,822 A | 11/1994 | McNeil |
| 5,407,642 A | 4/1995 | Lord |
| D367,526 S | 2/1996 | Bignon |
| D367,924 S | 3/1996 | Patel et al. |
| 5,520,921 A | 5/1996 | Chalifoux |
| D373,626 S | 9/1996 | Dente et al. |
| D375,350 S | 11/1996 | Patel et al. |
| 5,595,194 A | 1/1997 | Talbot |
| D380,258 S | 6/1997 | Muller et al. |
| 5,651,522 A | 7/1997 | Davis et al. |
| 5,683,285 A | 11/1997 | Wong |
| 5,695,692 A | 12/1997 | Kennedy |
| 5,704,832 A | 1/1998 | Borrell |
| D390,941 S | 2/1998 | Cessaroni et al. |
| D392,032 S | 3/1998 | Zaragoza et al. |
| 5,725,152 A | 3/1998 | Akyu |
| 5,762,549 A | 6/1998 | Scheuer et al. |
| 5,780,527 A | 7/1998 | O'Leary |
| 2,794,767 A | 8/1998 | Wilson |
| 5,820,791 A | 10/1998 | Canale |
| D400,662 S | 11/1998 | Davis |
| 5,845,847 A | 12/1998 | Martin et al. |
| 5,860,552 A | 1/1999 | Culhane et al. |
| 5,861,128 A | 1/1999 | Vick et al. |
| D404,957 S | 2/1999 | Cheris et al. |
| 5,871,765 A | 2/1999 | Johnson et al. |
| D410,540 S | 6/1999 | Pinchuk |
| D411,002 S | 6/1999 | Farmer |
| D415,267 S | 10/1999 | Kauzlarich et al. |
| D415,268 S | 10/1999 | Farmer |
| 5,988,520 A | 11/1999 | Bitner |
| D417,727 S | 12/1999 | Christianson |
| 6,044,202 A | 3/2000 | Junkel |
| D424,677 S | 5/2000 | Chen |
| D425,190 S | 5/2000 | Morikawa |
| 6,111,055 A | 8/2000 | Berger et al. |
| 6,123,906 A | 9/2000 | Farmer |
| 6,123,935 A * | 9/2000 | Wefler et al. ............... 424/76.1 |
| D432,222 S | 10/2000 | Rymer et al. |
| D435,694 S | 12/2000 | Lebherz |
| D437,038 S | 1/2001 | Chuan |
| D437,041 S | 1/2001 | Eisenbraun |
| 6,190,607 B1 | 2/2001 | Farmer |
| 6,191,197 B1 | 2/2001 | Wang et al. |
| 6,202,938 B1 | 3/2001 | Collier |
| D440,294 S | 4/2001 | Bilek |
| D441,441 S | 5/2001 | Upson |
| 6,264,887 B1 | 7/2001 | Farmer |
| 6,291,371 B1 | 9/2001 | Shefer et al. |
| 6,309,715 B1 | 10/2001 | Lindauer et al. |
| 6,325,475 B1 | 12/2001 | Hayes et al. |
| D454,190 S | 3/2002 | Trocola |
| 6,357,260 B1 | 3/2002 | Lutz |
| 6,374,044 B1 | 4/2002 | Freidel |
| 6,375,966 B1 | 4/2002 | Maleeny et al. |
| 6,379,689 B1 | 4/2002 | Aguadisch |
| 6,391,398 B1 | 5/2002 | Pesu et al. |
| 6,416,043 B1 | 7/2002 | Elsenbraun |
| 6,514,467 B1 | 2/2003 | Bulsink et al. |
| D472,968 S | 4/2003 | Christianson |
| D478,379 S | 8/2003 | Talenton et al. |
| D478,973 S | 8/2003 | Wagner |
| D479,592 S | 9/2003 | Lammel et al. |
| D485,343 S | 1/2004 | Wu |
| D487,504 S | 3/2004 | Yuen |
| 6,712,286 B2 | 3/2004 | Baxter et al. |
| D488,214 S | 4/2004 | Quantin |
| D488,548 S | 4/2004 | Lablaine |
| D491,257 S | 6/2004 | Picken |
| D491,798 S | 6/2004 | Buthier |
| D496,720 S | 9/2004 | Dudley |
| 6,800,252 B1 | 10/2004 | Jedzinski |
| 6,830,733 B2 | 12/2004 | Stanley, III |
| 6,885,811 B2 | 4/2005 | He et al. |
| D504,943 S | 5/2005 | Dudley |
| D507,341 S | 7/2005 | Taylor |
| D511,568 S | 11/2005 | Wheatley |
| D514,679 S | 2/2006 | Wheatley |
| D515,192 S | 2/2006 | Smith et al. |
| 7,025,283 B2 | 4/2006 | Torres |
| 7,055,764 B1 | 6/2006 | Martinez et al. |
| 7,061,386 B2 | 6/2006 | Seresini |
| 7,137,570 B2 | 11/2006 | Wheatley et al. |
| D535,376 S | 1/2007 | Michaels et al. |
| D535,379 S | 1/2007 | Hundertmark |
| 7,159,792 B2 | 1/2007 | Wheatley et al. |
| D544,080 S | 6/2007 | Carlson |
| D544,084 S | 6/2007 | Michaels et al. |
| D544,594 S | 6/2007 | Zobele |
| D544,953 S | 6/2007 | Kee |
| D546,432 S | 7/2007 | Hundertmark |
| 7,243,859 B2 | 7/2007 | Caserta et al. |
| D548,317 S | 8/2007 | Newton et al. |
| D550,345 S | 9/2007 | Weggelaar |
| D551,333 S | 9/2007 | Wu |
| 7,285,248 B2 | 10/2007 | Yamamoto et al. |
| D554,746 S | 11/2007 | Davis et al. |
| 7,293,719 B2 | 11/2007 | Wheatley et al. |
| D565,162 S | 3/2008 | Carlson |
| 7,344,123 B2 | 3/2008 | Pankhurst et al. |
| D565,715 S | 4/2008 | Wu |
| D573,706 S | 7/2008 | Zlotnik et al. |
| D574,941 S | 8/2008 | Weggelaar |
| 7,441,360 B2 | 10/2008 | Christianson et al. |
| D580,039 S | 11/2008 | Zlotnik et al. |
| D585,129 S | 1/2009 | Huang |
| D585,971 S | 2/2009 | Carrizales |
| D591,415 S | 4/2009 | Wu |
| D593,670 S | 6/2009 | Valentino et al. |
| D594,953 S | 6/2009 | King et al. |
| D594,954 S | 6/2009 | Wheatley |
| 7,544,332 B2 | 6/2009 | De Silva et al. |
| D597,645 S | 8/2009 | Thompson |
| D598,531 S | 8/2009 | Irvin |
| D604,825 S | 11/2009 | Brandenburg |
| D607,983 S | 1/2010 | Irvin |
| 7,651,666 B2 | 1/2010 | Adair et al. |
| 7,670,566 B2 | 3/2010 | Adair et al. |
| 7,687,037 B2 | 3/2010 | Wheatley et al. |

(56) References Cited

U.S. PATENT DOCUMENTS

| | | | |
|---|---|---|---|
| 7,687,038 | B2 | 3/2010 | Wheatley |
| D614,277 | S | 4/2010 | Hsiao |
| D619,692 | S | 7/2010 | Hami et al. |
| D619,693 | S | 7/2010 | Hami et al. |
| D619,694 | S | 7/2010 | Hami et al. |
| D620,573 | S | 7/2010 | Hami et al. |
| D622,835 | S | 8/2010 | Mendheim |
| 7,780,094 | B2 | 8/2010 | Caserta et al. |
| D625,798 | S | 10/2010 | Hami et al. |
| D629,881 | S | 12/2010 | Valentino et al. |
| D631,534 | S | 1/2011 | Kajizuka |
| D631,954 | S | 2/2011 | Bertassi et al. |
| D633,610 | S | 3/2011 | Wu |
| D637,275 | S | 5/2011 | Baraky |
| D640,358 | S | 6/2011 | Irvin |
| D640,781 | S | 6/2011 | Brandenburg |
| D642,668 | S | 8/2011 | Lablaine |
| D645,949 | S | 9/2011 | Brandenburg et al. |
| D647,186 | S | 10/2011 | Chan et al. |
| D649,237 | S | 11/2011 | Bilko et al. |
| D650,892 | S | 12/2011 | Wheatley |
| D662,581 | S | 6/2012 | Savegnago |
| D667,100 | S | 9/2012 | Harkim |
| 2001/0051234 | A1 | 12/2001 | Ryan et al. |
| 2003/0097936 | A1 | 5/2003 | Maleeny et al. |
| 2003/0199421 | A1 | 10/2003 | Copfer |
| 2004/0197221 | A1 | 10/2004 | Stanley, III |
| 2004/0265164 | A1 | 12/2004 | Woo et al. |
| 2005/0084413 | A1 | 4/2005 | Stanley, III |
| 2005/0127538 | A1 | 6/2005 | Fabrega et al. |
| 2005/0169793 | A1 | 8/2005 | Wheatley et al. |
| 2006/0043216 | A1 | 3/2006 | Robinson |
| 2006/0078477 | A1 | 4/2006 | Althouse et al. |
| 2006/0196964 | A1 | 9/2006 | Wheatley et al. |
| 2006/0279008 | A1 | 12/2006 | Jursich |
| 2007/0057084 | A1 | 3/2007 | Vieira |
| 2007/0160492 | A1 | 7/2007 | Spector |
| 2007/0231508 | A1 | 10/2007 | Fand et al. |
| 2007/0290064 | A1 | 12/2007 | Majerowski et al. |
| 2008/0099576 | A1 | 5/2008 | Hart |
| 2008/0128925 | A1 | 6/2008 | Pankhurst et al. |
| 2008/0311315 | A1 | 12/2008 | Marlow |
| 2008/0311316 | A1 | 12/2008 | Marlow |
| 2009/0008411 | A1* | 1/2009 | Schumacher et al. ........ 222/175 |
| 2009/0010813 | A1 | 1/2009 | Wang et al. |
| 2009/0072045 | A1 | 3/2009 | Wheatley et al. |
| 2009/0173799 | A1 | 7/2009 | Litten-Brown et al. |
| 2010/0010409 | A1 | 1/2010 | Irvin |
| 2010/0019059 | A1* | 1/2010 | Bulsink et al. ................ 239/55 |
| 2010/0065654 | A1 | 3/2010 | Wheatley et al. |
| 2010/0187327 | A1 | 7/2010 | Irvin |
| 2010/0288847 | A1* | 11/2010 | Gruenbacher et al. .......... 239/34 |
| 2011/0108632 | A1 | 5/2011 | Brandenburg et al. |
| 2011/0110823 | A1 | 5/2011 | Wheatley |

FOREIGN PATENT DOCUMENTS

| | | |
|---|---|---|
| EP | 1 346 734 | 9/2003 |
| WO | WO 98/46284 | 10/1998 |
| WO | WO 00/24434 | 5/2000 |
| WO | WO 00/64498 | 11/2000 |
| WO | WO 02/35975 | 5/2002 |
| WO | WO 02/38029 | 5/2002 |
| WO | WO 2004/078219 | 9/2004 |
| WO | WO 2006/010282 | 2/2006 |
| WO | WO 2006/084160 | 8/2006 |
| ZA | 20004637 | 9/2000 |

OTHER PUBLICATIONS

Aromate E-News, Innovation in Novelty Fragrance, Http://209.85.173.104/seasrch?qcach . . . , accessed Oct. 8, 2008, 2 pages.
Ecrater, www.ecrater.com/product.hp?. . . , Yankee Candle Selects Two Scents Electric Fragrance Unit Macintosh/Home Sweet Home, accessed Oct. 2, 2008, 1 page.
http://decomodo.com/articles/categor/lighting/, Bamboo Pillar Candle, Jan. 8, 2008, 1 page.
http://shop.advanceautoparts.com/webapp/wcs/stores/servlet/product_6170795-P_N3004 . . . Advance Auto Part; Arometrics Dual-Scent Vent—Juicy Strawberry and Vanilla; 1 Page; accessed Dec. 10, 2010.
http://www.bestliquidations.com/Medo_Vent Frehser.htm; BestLiquidations.com; Medo Vent Fresh Air Fresheners; 2 pages; accessed Dec. 10, 2010.
Medo® Air Fresheners; Auto Expressions™ 2005 Product Catalog; 25 pages.
Pictures (3) of Medo® auto Expressions Vent™ Air Freshener distributed by SOPUS Products of Moorpark, CA 2003 copyright date on package.
Scents & Sprays, www.scentsandsprays.com/ya . . . , Yankee Autumn Bounty Electric 2 Home Air Fresheners, copyright 2001-2008 scentsandsprays.com, accessed Oct. 2, 2008, 1 page.
U.S. Appl. No. 13/191,966, filed Jul. 27, 2011; Aaron Irvin.
U.S. Appl. No. 12/378,121, filed Oct. 29, 2010; Aaron Irvin.
U.S. Appl. No. 12/915,924, filed Oct. 29, 2010; Nathaniel Finlay.
U.S. Appl. No. 12/915,983, filed Oct. 29, 2010; Alan J. Wheatley.
U.S. Appl. No. 12/916,038, filed Oct. 29, 2010; Aaron Irvin.
U.S. Appl. No. 12/979,763, filed Dec. 28, 2010; Aaron Irvin.
U.S. Appl. No. 12/979,795, filed Dec. 28, 2010; Aaron Irvin.
U.S. Appl. No. 12/979,813, filed Dec. 28, 2010; Aaron Irvin.
U.S. Appl. No. 29/378,112, filed Oct. 29, 2010; Nathaniel Finlay.
www.4imprint.com/EXEC/DETAIL/FROMPRODUCTGROUP/~SKU100300/~CA100300.htm, Hot Rod Vent Stick Air Freshener (it . . . , accessed Aug. 12, 2008, 2 pages.
www.autothing.com/Products/Air%20Fresheners/air%20freshener-clip.htm, Air Fresheners, Fresh Scents for you mobile Life, Clip-on Air Vent Clips rom Eagle o., Accessed Aug. 12, 2008, 1 page.
www.chicscents.com/Products.aspx Island Adventure Sandals; 2 pages; accessed Feb. 1, 2011.
www.chicscents.com/Products.aspx; Inspiration 3-D by Chic; 2 pages; accessed Feb. 1, 2011.
U.S. Appl. No. 13/282,035, filed Oct. 26, 2011; Nathaniel Finlay.
U.S. Appl. No. 13/359,726, filed Jan. 27, 2012; Aaron Irvin.
U.S. Appl. No. 29/415,358, filed Mar. 9, 2012; Aaron Irvin; Notice of Allowance issued May 29, 2012.
U.S. Appl. No. 12/693,543, filed Jan. 26, 2010; Aaron Irvin; office action dated Aug. 7, 2012.
U.S. Appl. No. 12/979,795, filed Dec. 28, 2010; Aaron Irvin; office action dated Sep. 13, 2012.
U.S. Appl. No. 12/979,813, filed Dec. 28, 2010; Aaron Irvin, office action dated Sep. 14, 2012.
U.S. Appl. No. 29/435,389, filed Oct. 23, 2012; Aaron Irvin; notice of allowance dated Mar. 1, 2013.
U.S. Appl. No. 12/979,690, filed Dec. 28, 2010; Alan J. Wheatley; office action dated Mar. 1, 2013.
U.S. Appl. No. 12/987,662, filed Jan. 10, 2011; Alan J. Wheatley; office action dated Mar. 21, 2013.
U.S. Appl. No. 12/979,601, filed Dec. 28, 2010; Alan J. Wheatley; office action dated Mar. 1, 2013.
U.S. Appl. No. 13/009,574, filed Jan. 19, 2011; Alan J. Wheatley notice of allowance dated Apr. 3, 2013.
U.S. Appl. No. 13/359,726, filed Jan. 27, 2012; Aaron Irvin; office action dated Apr. 5, 2013.
U.S. Appl. No. 12/979,763, filed Dec. 28, 2010; Aaron Irvin notice of allowance dated Apr. 15, 2013.
U.S. Appl. No. 12/987,662, filed Jan. 10, 2011; Alan J. Wheatley; notice of allowance dated Jun. 7, 2013.
U.S. Appl. No. 12/979,690, filed Dec. 28, 2010; Alan J. Wheatley; notice of allowance dated Jun. 10, 2013.
U.S. Appl. No. 12/979,601, filed Dec. 28, 2010; Alan J. Wheatley; notice of allowance dated Jun. 10, 2013.
U.S. Appl. No. 29/435,391, filed Oct. 23, 2012; Aaron Irvin, notice of allowance dated Jun. 18, 2013.
U.S. Appl. No. 12/979,763, filed Dec. 28, 2010; Aaron Irvin; office action dated Dec. 14, 2012.
U.S. Appl. No. 12/693,543, filed Jan. 26, 2010; Aaron Irvin; office action dated Dec. 18, 2012.

(56) References Cited

OTHER PUBLICATIONS

U.S. Appl. No. 12/979,795, filed Dec. 28, 2010; Aaron Irvin; office action dated Jan. 28, 2013.
U.S. Appl. No. 13/009,574, filed Jan. 19, 2011; Alan J. Wheatley; office action dated Jan. 11, 2013.

U.S. Appl. No. 12/979,813, filed Dec. 28, 2010; Aaron Irvin; office action dated Jan. 31, 2013.

U.S. Appl. No. 12/915,983, filed Oct. 29, 2010; Alan J. Wheatley; notice of allowance dated Feb. 20, 2013.

* cited by examiner

US 8,673,223 B1

FAN POWERED AIR FRESHENER AUTOMOBILE VISOR CLIP

CROSS-REFERENCE TO RELATED APPLICATIONS AND CLAIM OF PRIORITY

Priority of U.S. Provisional Patent Application Ser. No. 61/408,263, filed on Oct. 29, 2010, is claimed, and is herein incorporated by reference.

BACKGROUND

1. Field of the Invention

The present invention relates generally to air fresheners.

2. Related Art

Battery powered chemical dispersers have been proposed. See, for example, U.S. Pat. No. 7,285,248; and US Patent Publication No. 2009-0008411.

SUMMARY OF THE INVENTION

It has been recognized that it would be advantageous to develop an air freshener capable of providing a fragrant air flow in a vehicle independent of vehicle power.

The invention provides an air freshener including a housing and a clip coupled to the housing forming a gap between the clip and the housing capable of receiving an automobile visor therebetween through a clip opening. An air displacement mechanism is carried by the housing and includes a fan rotatably disposed in a fan cavity having an inlet and an outlet, a motor coupled to the fan to rotate the fan, a battery coupled to the motor to power the motor, and a switch coupled between the motor and the battery to selectively activate and deactivate the air displacement mechanism. A scent capsule is carried by the housing and has a chamber containing a fragrant material and has a permeable membrane through which a fragrance of the fragrant material can permeate over time. The permeable membrane is located adjacent the fan.

In addition, the invention provides an air freshener in combination with a visor of a vehicle. The air freshener includes a housing having a body with a cavity therein and a cover removably engaging the body and covering the cavity. The body provides four sides and the cover provides two sides including a bottom and a front with an inlet aperture in the housing and a front outlet vent aperture in the front. A flexible and resilient clip is coupled to the body opposite the bottom of the body and forms a gap between the clip and body receiving the visor therebetween through a clip opening opposite the front of the cover. An air displacement mechanism is carried by the body of the housing and includes a fan rotatably disposed in a fan cavity having an inlet and an outlet, a motor coupled to the fan to rotate the fan, a battery coupled to the motor to power the motor, and a switch coupled between the motor and the battery to selectively activate and deactivate the air displacement mechanism. A scent capsule is removably carried by the cover of the housing and has a chamber containing a fragrant material and has a substantially flat permeable membrane through which a fragrance of the fragrant material can permeate over time. The permeable membrane is located adjacent the fan. An air flow path is defined through the housing in through the inlet aperture, past the permeable membrane of the scent capsule, and out of the front outlet vent aperture. A movable button is movably carried by the front of the cover and located adjacent to and engageable with the switch of the air displacement mechanism. A light source is coupled to the battery and the switch. The button is at least translucent. The cover includes a scent capsule aperture and the scent capsule includes a clear dome with the fragrant material visible through the clear dome and the scent capsule aperture in the cover. The scent capsule further includes a perimeter flange circumscribing the clear dome with a size greater than the scent capsule aperture to retain the scent capsule.

Furthermore, the invention provides an air freshener including a housing with an inlet aperture and a front outlet vent aperture in a front. A clip is coupled to the body opposite the bottom of the body and forms a gap between the clip and body capable of receiving an automobile visor therebetween through a clip opening opposite the front of the cover. An air displacement mechanism is carried by the body of the housing and includes a fan rotatably disposed in a fan cavity having an inlet and an outlet, a motor coupled to the fan to rotate the fan, a battery coupled to the motor to power the motor, and a switch coupled between the motor and the battery to selectively activate and deactivate the air displacement mechanism. At least one scent capsule is removably carried by the housing and has a chamber containing a fragrant liquid and has a substantially flat permeable membrane through which a fragrance of the fragrant liquid can permeate over time. The permeable membrane is located adjacent the fan. The at least one scent capsule has an indentation forming a vessel on one side and a dome on the other side, with the vessel containing the fragrant liquid covered by the permeable membrane. The dome with the fragrant liquid therein is visible through a scent capsule aperture in the housing.

BRIEF DESCRIPTION OF THE DRAWINGS

Additional features and advantages of the invention will be apparent from the detailed description which follows, taken in conjunction with the accompanying drawings, which together illustrate, by way of example, features of the invention; and, wherein.

Reference will now be made to the exemplary embodiments illustrated, and specific language will be used herein to describe the same. It will nevertheless be understood that no limitation of the scope of the invention is thereby intended.

DETAILED DESCRIPTION OF EXAMPLE EMBODIMENT(S)

Definitions

The term "visor" is used herein to refer to a sun visor of a vehicle or an automobile that is typically pivotally coupled above the front wind screen and pivotal between an up and retracted generally horizontal orientation when not in use, and a down and extended generally vertical or inclined orientation when in use to block sunlight.

The terms "top" and "bottom" and "downwardly" and "upwardly" and the like are used herein relative to the air freshener device or housing thereof being coupled to the visor of a vehicle in the up and retracted generally horizontal orientation; while it is understood that the device or the housing can change orientation as the visor is pivoted.

The term "scent material" and "fragrant material" are used interchangeably herein to refer broadly to a material that carries a desired fragrance or scent, or even a neutralizing agent.

The term "clear dome" is used herein to refer to a dome that is clear or transparent, or that is at least translucent.

DESCRIPTION

As illustrated in FIGS. 1-10, an air freshener device, indicated generally at 10, in an example implementation in accordance with the invention is shown for use with a visor of a vehicle or automobile. It will be appreciated that the air freshener can be clipped or fastened to other structures in the vehicle or automobile, and can even be used in other areas where fragrance is desired. The air freshener can provide a desired and/or aesthetically pleasing scent, fragrance, aroma or neutralizing agent. Air fresheners are one example of a field that can benefit from the present invention.

Figure 9:
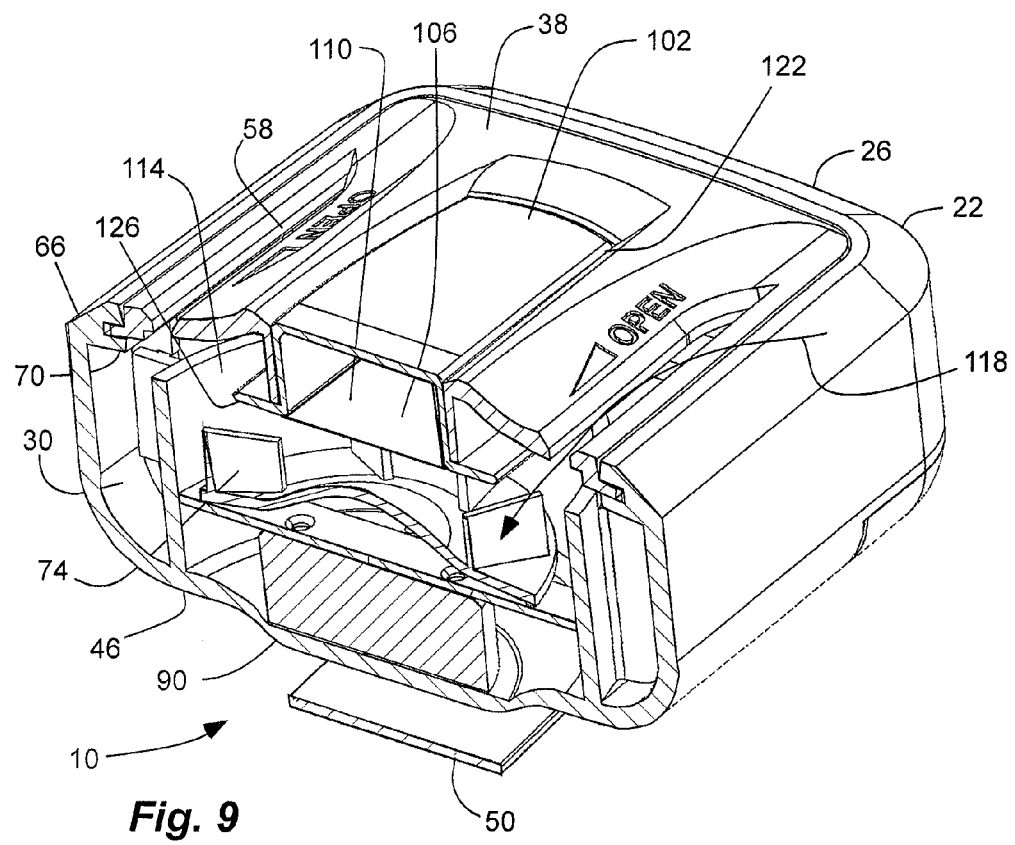
FIG. 9 is a forward and bottom cross-sectional perspective view of the air freshener of FIG. 1, taken along line 9 of FIG. 3.
Figure 10:
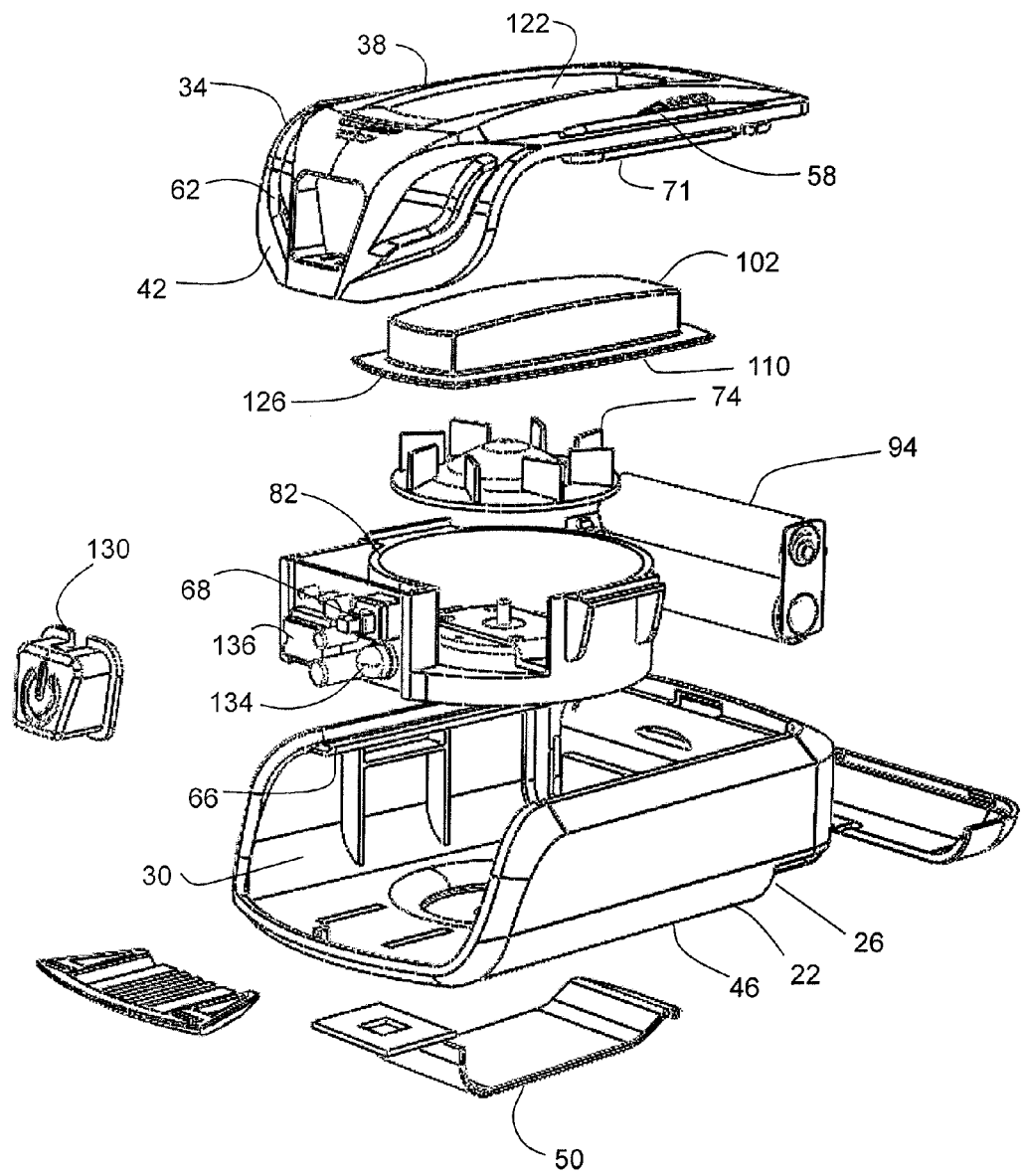
FIG. 10 is an exploded view of the air freshener of FIG. 1.

The air freshener has a housing 22 with a body 26 having a cavity 30 therein, and a cover 34 removably engaging the body and covering the cavity. The cover can form part of the body or the housing. The housing can have six sides, with the body providing four sides and the cover providing two sides. The housing can include a bottom 38 and a front 42, which can be provided by the cover. The housing and/or the body can also have a top 46 with a flexible and resilient clip 50. The clip can be coupled to the body opposite the bottom of the body and forming a gap between the clip and body capable of receiving an automobile visor therebetween through a clip opening 54 opposite the front 42 of the cover 34. Thus, the clip can define the top of the housing when clipped to a visor in the up and retracted generally horizontal orientation. The housing and/or the body can also provide opposite sides and a rear or back. The housing and/or the body can have an inlet aperture 58, such as a bottom aperture formed in the bottom 38 of the housing and/or the body. The inlet aperture 58 can be formed in the cover 34. The inlet aperture 58 can include one or more apertures. The front 42 of the housing and/or the body can have a front outlet vent aperture 62. The front outlet vent aperture 62 can be formed in the cover 34. The front outlet vent aperture 62 can include one or more apertures. The inlet aperture 58 can face downwardly, opposite the clip, while the front outlet vent aperture 62 can face forwardly towards a user. The housing and/or the body can be open on the bottom and the front to receive the cover, with the cover covering the bottom and the front. Opposite grooves 66 can be located on opposite sides of the body or open bottom thereof and oriented perpendicularly to the front. Opposite tabs 70 can be located on opposite sides of the cover 34 and slidably received within the opposite grooves 66, as shown in FIG. 9. Thus, the cover 34 can be coupled to the housing 22 and/or the body 26 by sliding the cover with the tabs in the grooves from the front. Similarly, the cover can be removed from the housing or body by sliding the cover towards the front. The cover can be removed to insert and/or replace a scent capsule, as described below. The clip 50 can include a flexible and resilient piece of metal with one end secured to the top 46 of the housing and/or body, and extending to a free end biased towards the top, but extending away from the top to form the clip opening 54. Alternatively, the clip can be pivotally coupled to the top, with a coil or leaf spring biasing a free end of the clip towards the housing and/or body, or top thereof.

An air displacement mechanism is carried by the body of the housing, or the housing, and disposed in the cavity 30 thereof. The air displacement mechanism includes a fan or a turbine 74 rotatably disposed in a fan cavity 78. The fan cavity 78 can have an inlet 82 and an outlet 86. A motor 90 is coupled to the fan to rotate the fan. A battery 94 is coupled to the motor to power the motor. A switch 98 is coupled between the motor and the battery to selectively activate and deactivate the air displacement mechanism. The fan can be a centrifugal fan with an impeller carrying blades and blowing air at a right angle to the intake of the fan. Alternatively, the fan can be an axial-flow fan with blades, such as propeller style blades, that force air to move parallel to the shaft about which the blades rotate. Alternatively, the fan can be a cross-flow or tangential fan.

The fan cavity 78 can be cylindrical with a cylindrical wall circumscribing a majority of the fan 78, and with the outlet 86 formed therein. The fan cavity can also have a top wall spanning the cylindrical wall opposite the inlet 82 and forming a cup-like cavity with the cylindrical wall. A frame can form the cup-like cavity, and can carry the motor, the switch, and control electronics or circuit board. The frame can be disposed in the cavity of the housing and/or body, and can have opposite tabs to engage the opposite sides of the body and/or housing. The frame can form an internal skeleton enclosed by the cover and the body which can form shells around the frame or skeleton. The inlet 82 of the fan cavity 78 can be in a plane perpendicular to the axis of the fan and motor, and a plane parallel with the rotation of the fan; while the outlet 86 of the fan or turbine cavity 78 can be perpendicular to the axis of the fan and motor and tangential with the rotation of the fan. The inlet 82 of the fan cavity 78 can face the bottom 38 of the cover 34, and thus the inlet aperture 58; while the outlet 86 of the fan cavity 78 can face the front 42 of the cover, and thus the front vent aperture 62. Thus, the inlet 82 can face downwardly and the outlet 86 can face forwardly. The fan or turbine 74 can displace air from outside the body or housing through the inlet aperture 58, and out the front vent aperture 62, towards the user.

Figure 1:
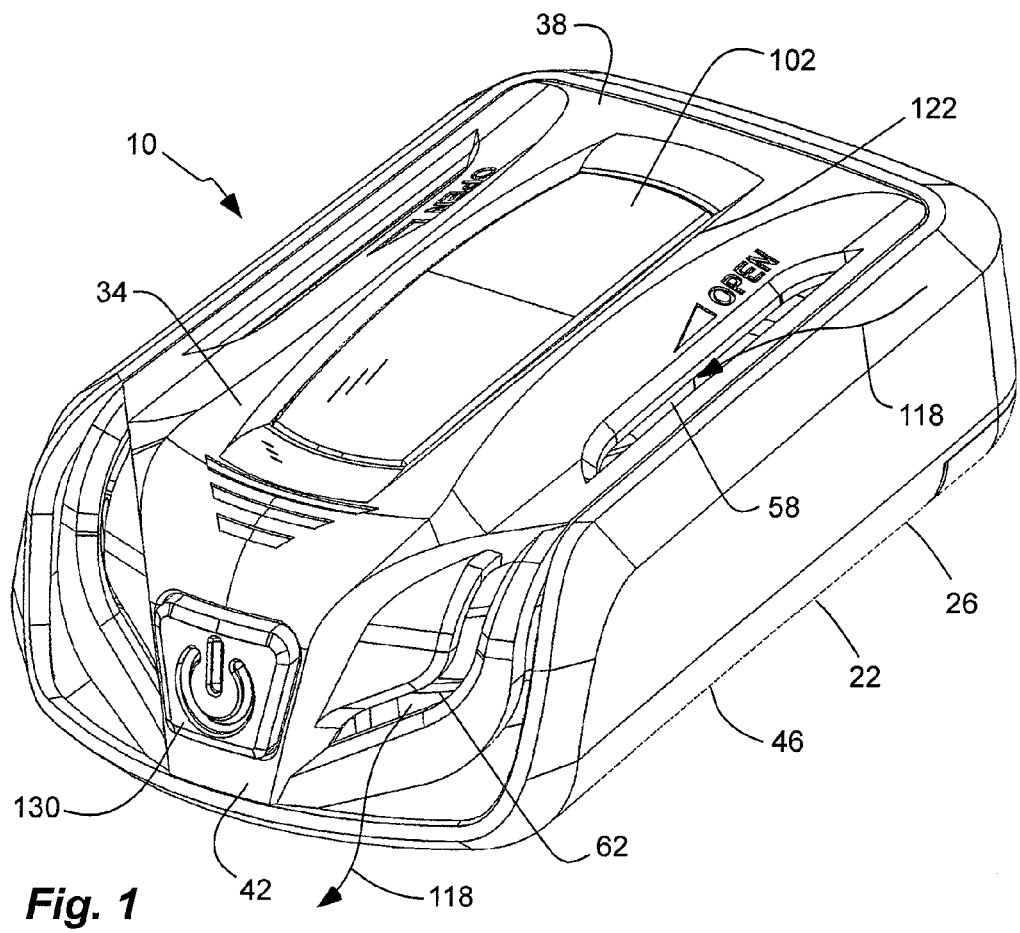
FIG. 1 is a forward and bottom perspective view of an air freshener in accordance with one embodiment of the present invention.
Figure 5A:
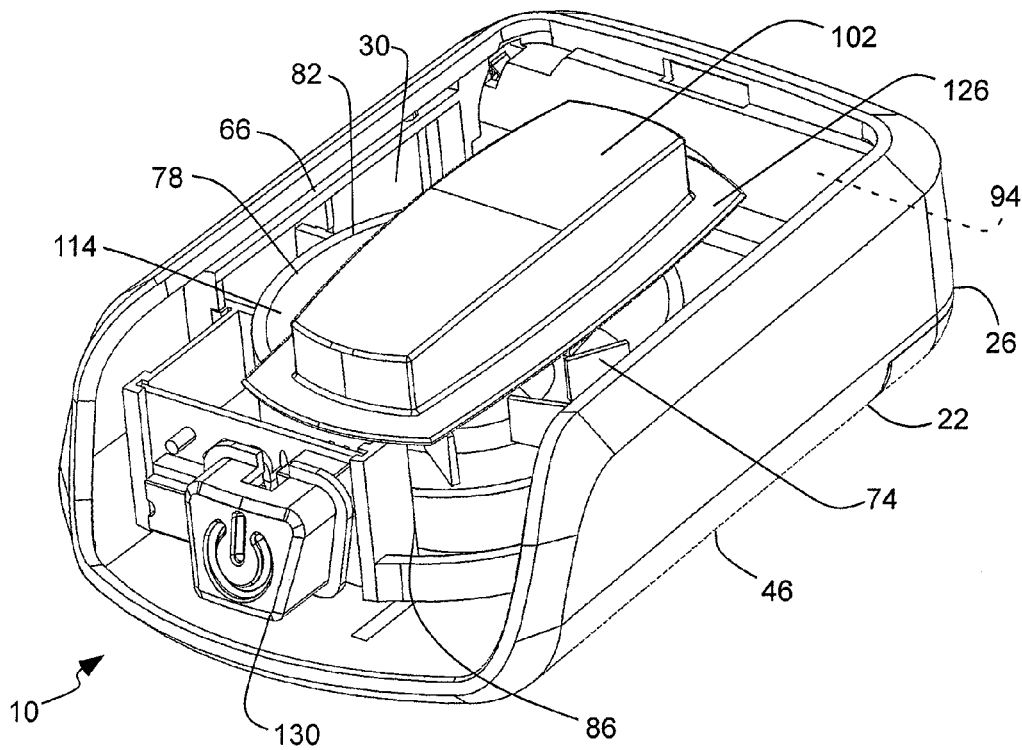
FIG. 5a is a forward and bottom perspective view of the air freshener of FIG. 1, with a cover removed, but with the scent capsule in place.
Figure 5B:
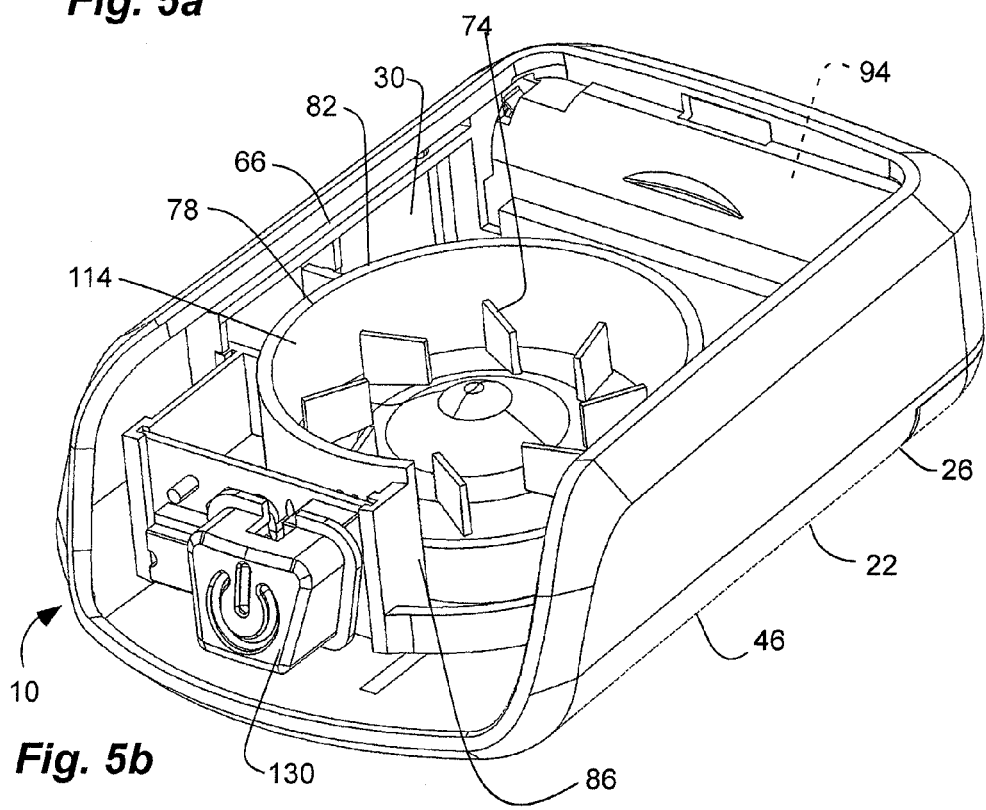
FIG. 5b is a forward and bottom perspective view of the air freshener of FIG. 1, with the cover and the scent capsule removed.
Figure 5C:
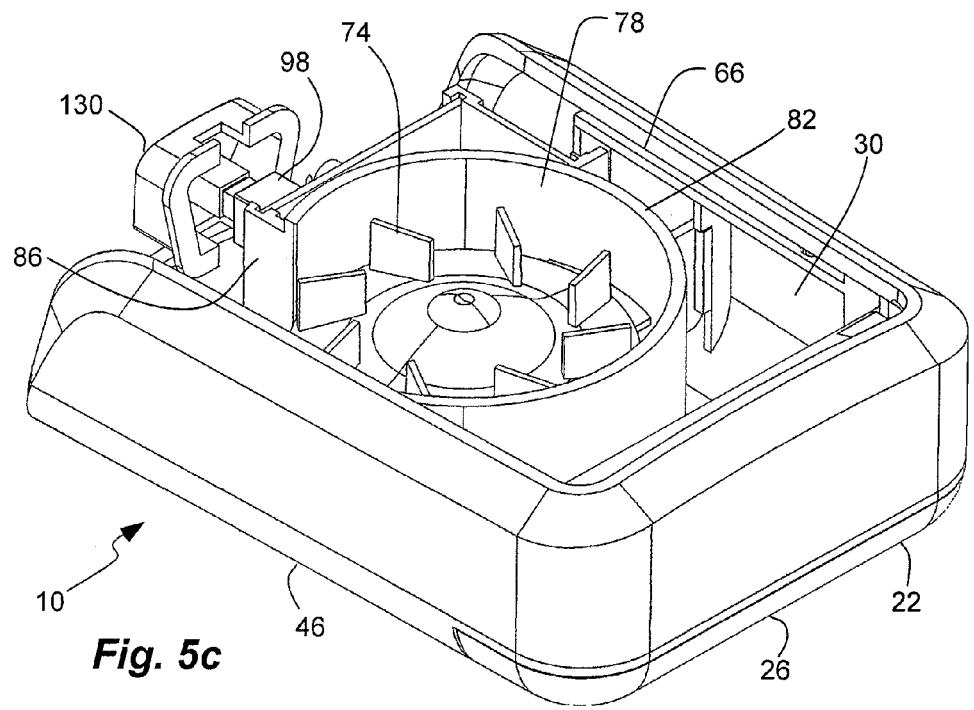
FIG. 5c is a rearward and bottom perspective view of the air freshener of FIG. 1, with the cover and the scent capsule removed.
Figure 6:
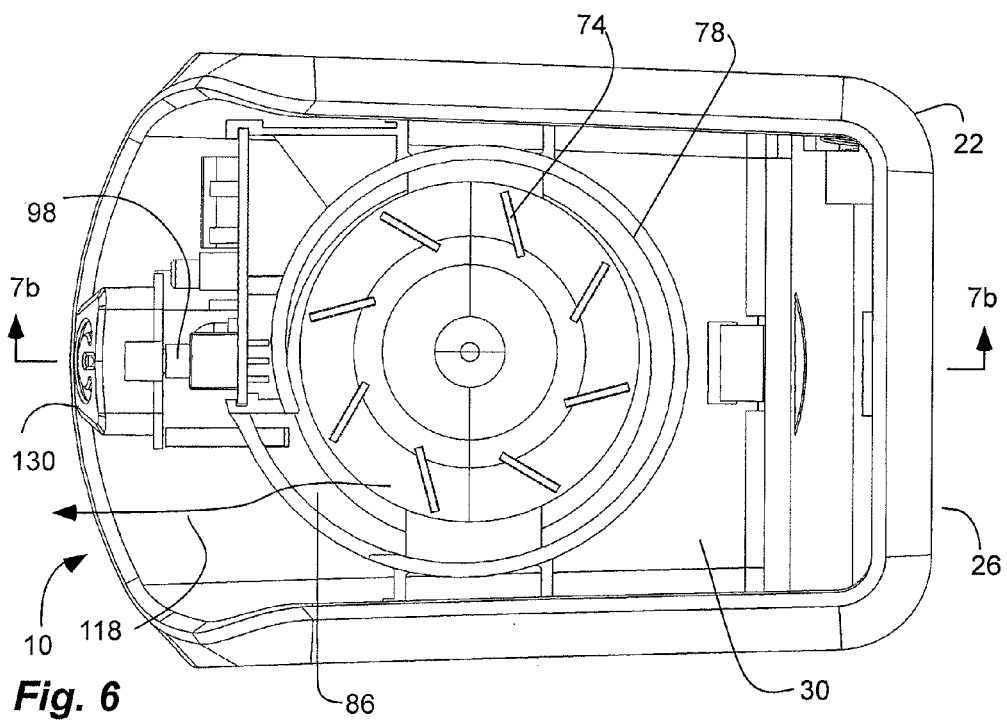
FIG. 6 is a bottom view of the air freshener of FIG. 1, with the cover and the scent capsule removed.

A scent capsule 102 can be removably carried by the cover 34 of the housing. The scent capsule 102 can be inserted into the housing and/or body along with the cover 34. Thus, scent capsules can be removed and replaced by removing and replacing the cover. The scent capsule 102 can have a chamber containing a fragrant material 106, and a substantially flat permeable membrane 110 through which a fragrance of the fragrant material can permeate over time. The fragrant material can be a liquid, such as a scented oil. The scent capsule can be formed by or can include a sheet, such as a transparent or translucent plastic, indented on one side to form the chamber or vessel to contain the fragrant material or liquid and covered by the permeable membrane, and with the indentation forming the transparent or translucent clear dome on the other side. The permeable membrane 110 can be substantially flat. The scent capsule can be oriented and the permeable membrane 110 can be located adjacent the inlet 82 to the fan cavity 78. The inlet 82 of the fan or turbine cavity 78 can be circular, and the scent capsule 102 or membrane 110 can be oblong or narrower than a diameter of the inlet to create one or more gaps 114 between the inlet and the membrane to accommodate air flow, as shown in FIGS. 5a and 9. Thus, the inlet 82 can be larger than the membrane 110 to form the gaps 114. The bottom of the cylindrical wall of the fan cavity 78 can be adjacent to the permeable membrane 110 and at least one gap 114 between the permeable membrane and the bottom of the cylindrical wall. In addition, an axis of the turbine or fan can be oriented perpendicularly to the substantially flat permeable membrane 110 of the scent capsule 102. The scent capsule forms a vessel covered by the permeable membrane with the fragrant material or liquid contained within the vessel, and with the permeable membrane facing upwardly towards the clip and opening. The membrane 110 can face upward towards the fan, while the fan cavity or inlet can face downwardly towards the membrane. Thus, fragrance can permeate the membrane 110 and into the fan or turbine cavity 78 or opening 82 thereof. An air flow path 118, as shown in FIGS. 1 and 9, can be defined through the housing, in through the inlet aperture 58, past the permeable membrane 110 of the scent capsule 102, in the inlet 82 of the fan or turbine cavity 78, out the outlet 86 of the fan or turbine cavity, and out of the front outlet vent aperture 62.

Figures 7A, 7B:
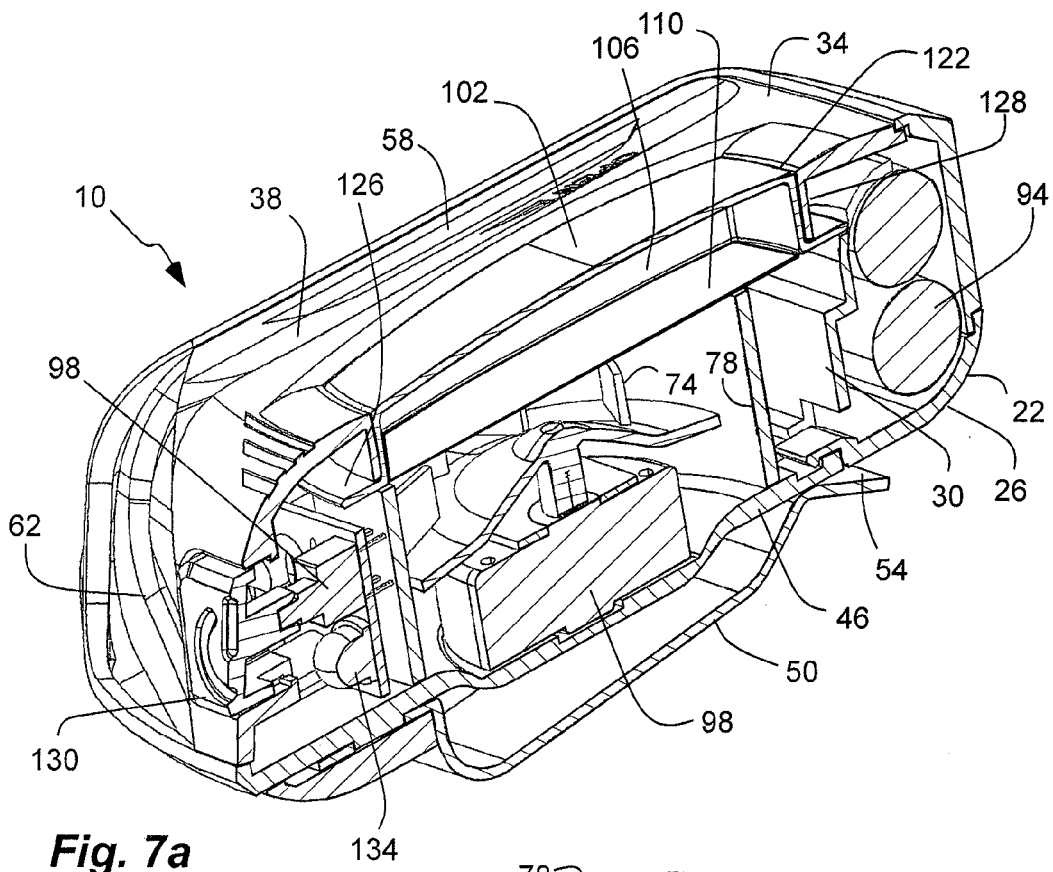
FIG. 7a is a forward and bottom cross-sectional perspective view of the air freshener of FIG. 1, taken along line 7a of FIG. 3.
FIG. 7b is a forward and bottom cross-sectional perspective view of the air freshener of FIG. 1, taken along line 7b of FIG. 6, with the cover and the scent capsule removed.
Figure 8:
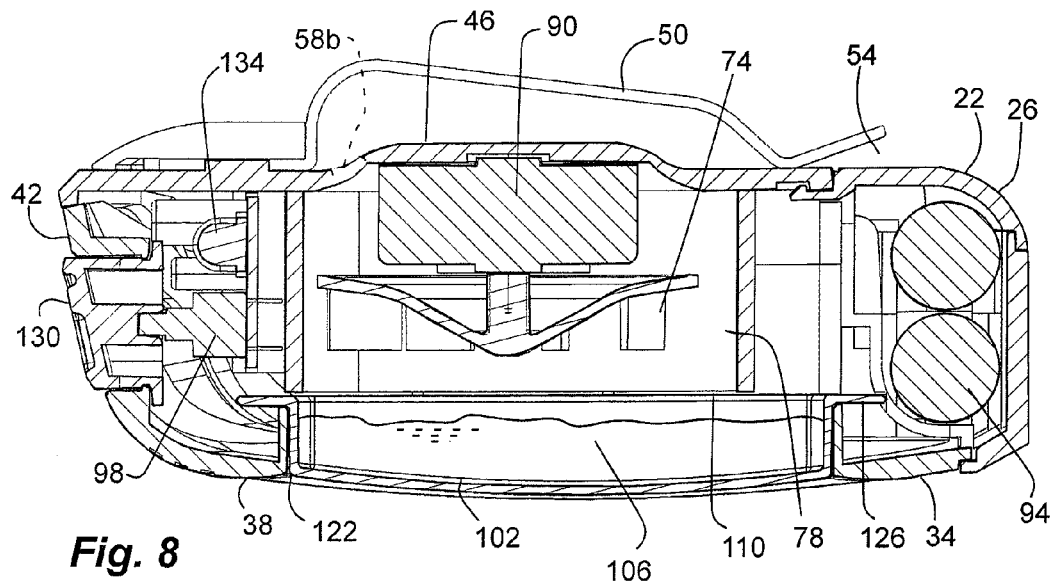
FIG. 8 is cross-sectional side view of the air freshener of FIG. 1, taken along line 7a of FIG. 3.

The cover 34, and/or bottom of the housing or the body, can include a scent capsule aperture 122 through which the scent capsule 102 or the dome thereof can be viewed. The scent capsule can include a clear dome with the fragrant material visible through the clear dome and the scent capsule aperture in the cover. The dome can be an inverted dome facing downwardly, or extending convexly, like a bottom of a transparent or translucent bowl. Thus, the amount of scent material remaining can be ascertained. The scent capsule can further including a perimeter flange 126 circumscribing the clear dome with a size greater than the scent capsule aperture to retain the scent capsule. The cover 34 can include a recess 128 or elongated aperture, as shown in FIG. 7a, receiving the chamber, vessel, or dome of the scent capsule 102 so that the scent capsule can move with the cover. The scent capsule aperture 122 can be formed in a bottom of the recess 128, such that the recess 128 is an elongated aperture through the cover. Thus, the liquid or fragrant material in the chamber, vessel, or dome, is visible through the aperture. The flange 126 of the scent capsule can maintain the scent capsule in the recess or aperture. The thickness or height of the scent capsule can be less than or equal to a depth of the recess so that a bottom of the scent capsule (or chamber, vessel, or dome) does not protrude through the scent capsule aperture 122 or recess, and so that the cover protects the scent capsule (or chamber, vessel or dome). Alternatively, the chamber, vessel or dome of the scent capsule can protrude from the cover, and the fragrant material or portion thereof can be disposed outside the cover, and thus the housing and body, for increased visibility. The clear come can be transparent or translucent.

A movable button 130 can be movably carried by the front 42 of the cover 34 and located adjacent to and engageable with the switch 98 of the air displacement mechanism. The button 130 can also be removed and replaced along with the cover 34. The button 130 can cover the switch 98. A light source 134, as shown in FIGS. 7a and 7b, can be coupled to the battery and switch. The button 130 can be at least translucent so that it lights up via the light source 134 when the air freshener is on. The air freshener can have control electronics and/or a circuit board with a timer circuit 136 coupled to the switch to deactivate the fan or the turbine after a predetermined amount of time. Thus, a user can push the button a single time for a predetermined period of operation of the fan, without worrying about needing to turn the fan off. In addition, the switch can be a push button switch where sequential pushing sequentially activates and deactivates the fan or the turbine, so that the user can deactivate the fan if desired. The button 130 can push against the switch. In addition, the clear dome, the permeable membrane, and the fragrant material of liquid can be transparent or translucent; and the light source can be located to emit light through the dome, membrane and fragrant material that is visible through the scent capsule aperture to facilitate visibility of the remaining scent material.

Figure 2:
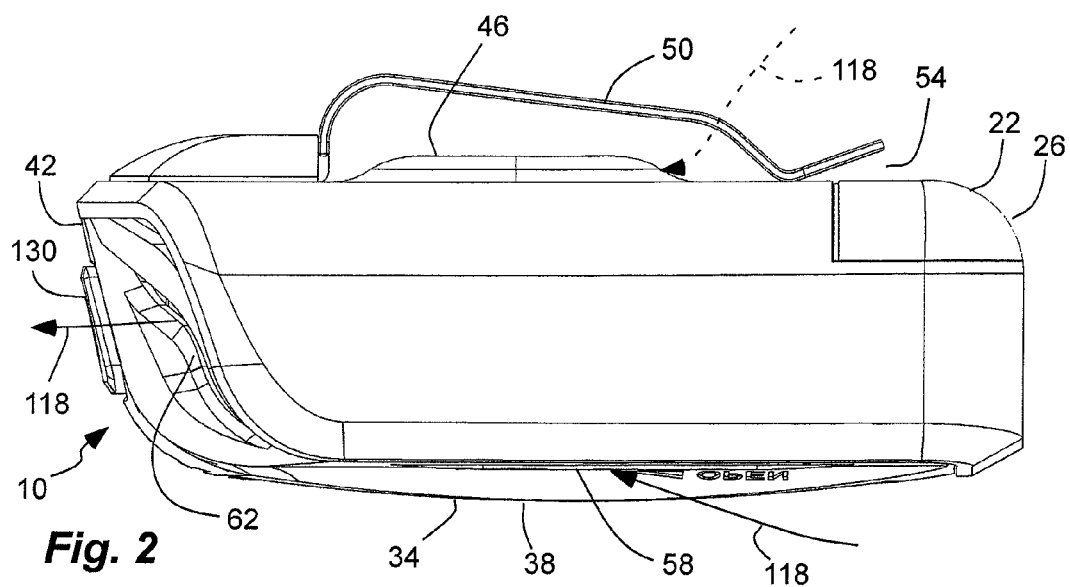
FIG. 2 is a side view of the air freshener of FIG. 1.
Figure 3:
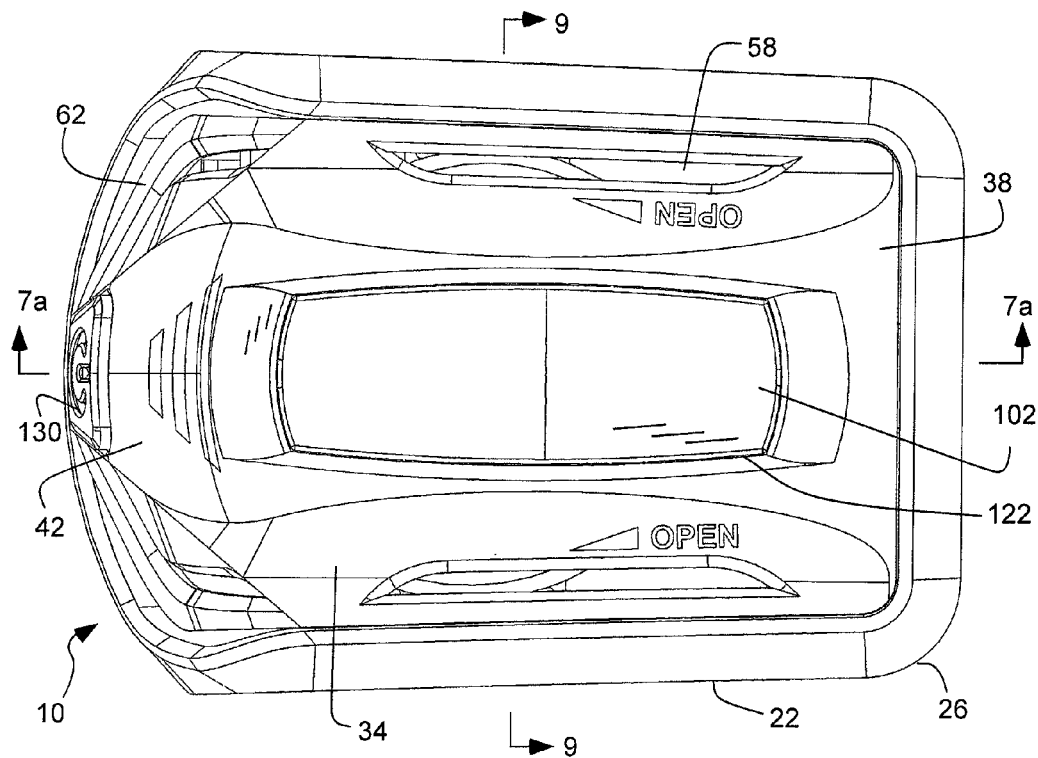
FIG. 3 is a bottom view of the air freshener of FIG. 1.
Figure 4:
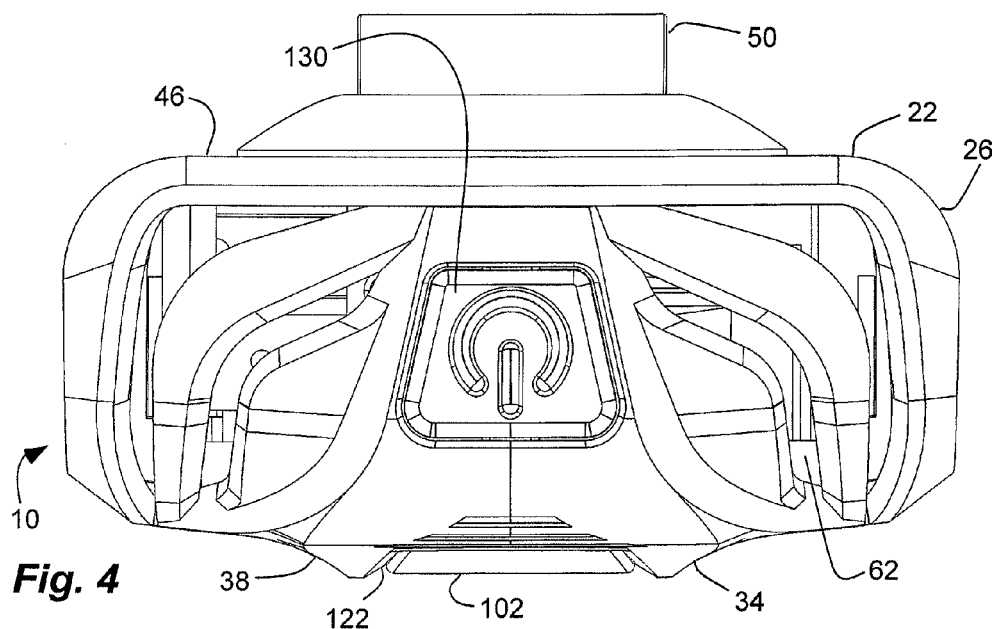
FIG. 4 is a front view of the air freshener of FIG. 1.

Although the above air freshener has been shown and described with inlet apertures 58 in the bottom 38 and/or the cover 34, the inlet apertures (indicate by 58b in dashed lines in FIG. 8) can also be formed in the top 46 of the body defining an air flow path, indicated by dashed lines 118 in FIG. 2, through a top of the housing and/or body. The inlet apertures 58b can face upwardly, towards the clip. In such a case, the fan cavity can be open, or have openings, in the top thereof, with the cylindrical wall being open or substantially open at both longitudinal ends.

Figure 11:
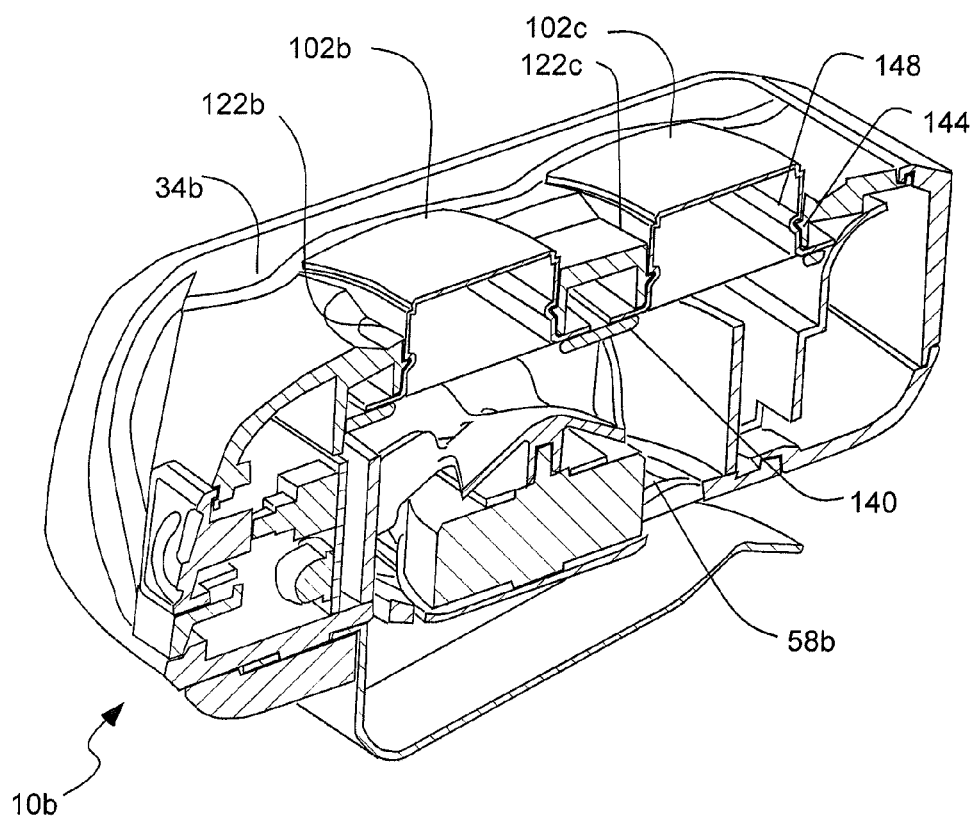
FIG. 11 is a forward and bottom cross-sectional perspective view of another air freshener in accordance with another embodiment of the present invention.

Although the above air freshener has been shown and described with a single scent capsule, the air freshener can be provided with two or more scent capsules, having different and complimentary scents. Referring to FIG. 11, another air freshener device, indicated generally at 10b, in accordance with another embodiment of the present invention is shown; and which is similar in many respects to that described above; and which description is herein incorporated by reference. The air freshener 10b can have two scent capsules 102b and 102c carried by the cover 34b and each extending into different apertures 122b and 122c. The scent capsules can be retained against the cover by a retainer plate 140. The retainer plat can have a pair of apertures corresponding to the membranes of the scent capsules. The scent capsules can have different fragrances. The inlet apertures 58b can be formed in the top of the body or housing.

In addition, the scent capsules can be retained in the apertures by detents, forming mating protrusions and indentations. For example, a protrusion 144 can be formed on the inner surface of the aperture, and extending into an indentation 148 on a side surface of the dome of the capsule.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The invention claimed is:

1. An air freshener device, comprising:
    a) a housing having a scent capsule aperture in a bottom thereof;
    b) a clip coupled to the housing forming a gap between the clip and the housing capable of receiving an automobile visor therebetween through a clip opening;

c) an air displacement mechanism carried by the housing including a fan rotatably disposed in a fan cavity having an inlet and an outlet, a motor coupled to the fan to rotate the fan, a battery coupled to the motor to power the motor, and a switch coupled between the motor and the battery to selectively activate and deactivate the air displacement mechanism;
d) a scent capsule carried by the housing and having a vessel enclosed by a permeable membrane and containing a fragrant material in the vessel that can permeate through the permeable membrane over time, the permeable membrane located adjacent the fan;
e) the vessel having an inverted transparent dome forming a bowl;
g) the bowl extending into the scent capsule aperture of the housing; and
h) a light source disposed in the housing and coupled to the battery and switch, and located to emit light through the fragrant material and the bowl.

2. A device in accordance with claim 1, wherein the housing has a body with a cavity therein and a cover removably engaging the body and covering the cavity, the body providing four sides and the cover providing two sides including the bottom opposite the clip and a front opposite the clip opening, with an inlet aperture in the housing and a front outlet vent aperture in the front; wherein the housing has an air flow path defined through the housing in through the inlet aperture, past the permeable membrane of the scent capsule, and out of the front outlet vent aperture.

3. A device in accordance with claim 2, further comprising:
a movable button movably carried by the front of the cover and located adjacent to and engageable with the switch of the air displacement mechanism, and the button being at least translucent.

4. A device in accordance with claim 2, wherein the scent capsule is carried by the cover; and wherein the cover includes the scent capsule aperture, the scent capsule further including a perimeter flange circumscribing the dome with a size greater than the scent capsule aperture to retain the scent capsule.

5. A device in accordance with claim 1, further comprising:
a timer circuit coupled to the switch to deactivate the fan after a predetermined amount of time.

6. A device in accordance with claim 1, wherein the switch is a push button switch where sequential pushing sequentially activates and deactivates the fan.

7. A device in accordance with claim 1, wherein an axis of the fan is oriented perpendicularly to the permeable membrane of the scent capsule.

8. A device in accordance with claim 1, wherein the inlet of the fan cavity is adjacent to the permeable membrane and the membrane is narrower than the inlet to form at least one gap between the permeable membrane and the inlet.

9. A device in accordance with claim 1, wherein the scent capsule further comprises:
two scent capsules disposed adjacent one another and each containing a different fragrance.

10. A device in accordance with claim 9, further comprising:
a retainer plate removably securing the two scent capsules to the housing, the retainer plate having a pair of apertures corresponding to the membranes of the two scent capsules.

11. An air freshener device in combination with a visor of a vehicle, the device comprising:
a) a housing having a body with a cavity therein and a cover removably engaging the body and covering the cavity, the body providing four sides and the cover providing two sides including a bottom and a front with an inlet aperture in the housing and a front outlet vent aperture in the front;
b) a flexible and resilient clip coupled to the body opposite the bottom of the body and forming a gap between the clip and body receiving the visor therebetween through a clip opening opposite the front of the cover;
c) an air displacement mechanism carried by the body of the housing including a fan rotatably disposed in a fan cavity having an inlet and an outlet, a motor coupled to the fan to rotate the fan, a battery coupled to the motor to power the motor, and a switch coupled between the motor and the battery to selectively activate and deactivate the air displacement mechanism;
d) the cover having a recess and a scent capsule aperture;
e) a scent capsule removably carried by the cover of the housing and having a vessel formed by a clear dome enclosed by a substantially flat permeable membrane and containing a fragrant material that can permeate through the permeable membrane over time, the permeable membrane located adjacent the fan;
f) an air flow path defined through the housing in through the inlet aperture, past the permeable membrane of the scent capsule, and out of the front outlet vent aperture;
g) a light source coupled to the battery and the switch;
h) the clear dome being inverted to face downwardly and form a bowl received in the recess of the cover;
i) the bowl extending into the scent capsule aperture; and
j) the light source being located to emit light through the fragrant material and the bowl.

12. A device in accordance with claim 11, further comprising:
a timer circuit coupled to the switch to deactivate the fan after a predetermined amount of time.

13. A device in accordance with claim 11, wherein the switch is a push button switch where sequential pushing sequentially activates and deactivates the fan.

14. A device in accordance with claim 11, wherein an axis of the fan is oriented perpendicularly to the substantially flat permeable membrane of the scent capsule.

15. A device in accordance with claim 11, wherein the fragrant material is a liquid contained within the vessel with the permeable membrane facing upwardly towards the clip.

16. A device in accordance with claim 11, wherein the inlet of the fan cavity is adjacent to the permeable membrane and the membrane is narrower than the inlet to form at least one gap between the permeable membrane and the inlet.

17. A device in accordance with claim 11, wherein the scent capsule further comprises:
two scent capsules disposed adjacent one another and each containing a different fragrance.

18. A device in accordance with claim 17, further comprising:
a retainer plate removably securing the two scent capsules to the cover, the retainer plate having a pair of apertures corresponding to the substantially flat permeable membranes of the two scent capsules.

19. An air freshener device, comprising:
a) a housing with an inlet aperture and a front outlet vent aperture in the front and a scent capsule aperture in a bottom of the housing;
b) a clip coupled to the body forming a gap between the clip and body capable of receiving an automobile visor therebetween through a clip opening opposite the front of the cover;

c) an air displacement mechanism carried by the body of the housing including a fan rotatably disposed in a fan cavity having an inlet and an outlet, a motor coupled to the fan to rotate the fan, a battery coupled to the motor to power the motor, and a switch coupled between the motor and the battery to selectively activate and deactivate the air displacement mechanism;

d) at least one scent capsule removably carried by the housing and having a transparent plastic sheet with an indentation on one side forming a vessel containing a fragrant liquid and covered by a substantially flat permeable membrane through which a fragrance of the fragrant liquid can permeate over time, the permeable membrane located adjacent the fan, and the indentation forming a transparent dome on the other side of the sheet from the vessel; and e) the dome with the fragrant liquid therein protruding into the scent capsule aperture in the housing.

20. A device in accordance with claim 19, wherein the at least one scent capsule further comprises: two scent capsules disposed adjacent one another and each containing a different fragrance; and further comprising a retainer plate removably securing the two scent capsules to the housing, the retainer plate having a pair of apertures corresponding to the membranes of the two scent capsules.

21. A device in accordance with claim 1, wherein the vessel comprises a transparent plastic sheet with an indentation on one side forming the vessel containing the fragrant liquid covered by the permeable membrane, and the indentation forming a transparent dome on the other side of the sheet from the vessel.

22. A device in accordance with claim 11, wherein the vessel comprises a transparent plastic sheet with an indentation on one side forming the vessel containing the fragrant liquid covered by the permeable membrane, and the indentation forming the clear dome on the other side of the sheet from the vessel.

23. A device in accordance with claim 19, further comprising a light source disposed in the housing, and located to emit light through the fragrant liquid and the dome.

\* \* \* \* \*